United States Patent [19]
Michaels

[11] Patent Number: 5,389,676
[45] Date of Patent: Feb. 14, 1995

[54] VISCOUS SURFACTANT EMULSION COMPOSITIONS

[75] Inventor: Edwin B. Michaels, Milford, Conn.

[73] Assignee: E. B. Michaels Research Associates, Inc., Milford, Conn.

[21] Appl. No.: 121,277

[22] Filed: Sep. 13, 1993

Related U.S. Application Data

[63] Continuation-in-part of Ser. No. 673,631, Mar. 22, 1991, Pat. No. 5,244,652, and a continuation-in-part of Ser. No. 673,784, Mar. 22, 1991, Pat. No. 5,314,917.

[51] Int. Cl.$^6$ .................. A61K 31/205; A61K 31/13
[52] U.S. Cl. ..................................... 514/556; 514/644
[58] Field of Search ............................. 514/556, 644

[56] References Cited

U.S. PATENT DOCUMENTS

| | | | |
|---|---|---|---|
| 2,888,383 | 5/1959 | Byrne | 424/54 |
| 3,202,714 | 8/1965 | Zimmerer | 260/584 |
| 3,223,647 | 12/1965 | Drew | 252/137 |
| 3,898,186 | 8/1975 | Mermelstein | 252/528 |
| 3,976,765 | 8/1976 | Nachtigal | 424/54 |
| 4,062,976 | 1/1977 | Michaels | 424/319 |
| 4,075,350 | 2/1978 | Michaels | 424/316 |
| 4,093,711 | 6/1978 | Blackburne | 424/54 |
| 4,107,328 | 7/1978 | Michaels | 424/316 |
| 4,117,108 | 9/1978 | Shapiro | 424/54 |
| 4,130,637 | 12/1978 | Bauman | 424/54 |
| 4,145,436 | 3/1979 | Michaels | 424/273 |
| 4,183,952 | 1/1980 | Michaels | 424/316 |
| 4,207,198 | 6/1980 | Kenkare | 252/117 |
| 4,209,504 | 6/1980 | Harth | 424/54 |
| 4,209,533 | 6/1980 | Gilbertson | 424/59 |
| 4,212,856 | 7/1980 | Hoyles | 424/52 |
| 4,213,961 | 7/1980 | Curtis | 424/54 |
| 4,215,144 | 7/1980 | Thiele | 424/318 |
| 4,219,541 | 8/1980 | Schmid | 424/54 |
| 4,439,355 | 3/1984 | Kenkare | 252/541 |
| 4,451,385 | 5/1984 | Tauas | 252/132 |
| 4,490,353 | 12/1984 | Crawford | 424/52 |
| 4,528,182 | 7/1985 | Curtis | 424/54 |
| 4,554,097 | 11/1985 | Schebece | 252/542 |
| 4,564,520 | 1/1986 | Ehrl | 424/70 |
| 4,832,871 | 5/1989 | Bade | 252/546 |
| 4,839,158 | 6/1989 | Michaels | 424/54 |
| 5,244,652 | 9/1993 | Michaels | 424/54 |

FOREIGN PATENT DOCUMENTS

| | | |
|---|---|---|
| 0231816 | 1/1987 | European Pat. Off. |
| 3706484 | 9/1988 | Germany |
| 1160485 | 8/1969 | United Kingdom |
| 8704922 | 8/1987 | WIPO |

OTHER PUBLICATIONS

A. M. Corner et al. VII International Conference of Aids, Florence, Italy, Jun. 16–21, 1991 Stn. accession No. 91:446745.
A. M. Corner et al. Journal of Clinical Dentistry 2(2):34–38 (1990).
A. M. Corner et al. Antimicrobial Agents and Chemotherapy 32 (3):350–353 (1988).
Chemical Abstract 100(15): 116374w (1984).
Chemical Abstract 99(13): 98853x (1983).
Chemical Abstracts 111:99431m (1989).
Chemical Abtracts 115:150372e (1991).
Accepted Dental Therapeutics American Dental Associates, Chicago, 1979; pp. 268–269.
Hart, J. R. et al. J. Soc. Cosmet, Chem. vol. 31: 223–236 (Sep./Oct. 1980).
Tanzer et al. Antimicrobial Agents and Chemotherapy vol. 13, No. 6, 1044–1045, Jun. 1978.

(List continued on next page.)

*Primary Examiner*—Johann Richter
*Assistant Examiner*—Rebecca Cook
*Attorney, Agent, or Firm*—Ladas & Parry

[57] ABSTRACT

Antiinfective water-in-oil or oil-in-water emulsions comprising amphoteric surfactants of betaines and amine oxides, hydrophobic materials and emulsion aids.

10 Claims, No Drawings

OTHER PUBLICATIONS

Tanzer et. al. Antimicrobial Agents and Chemotherapy vol. 12. No. 6, 721–729, 1977.

Patent Abstracts of Japan, vol. 8, No. 71. (C217) [1508] Apr. 3, 1984 & JP-A-58 225007 Dec. 27, 1983.

Corner, A. M. et al. Abstract 407 Journal of Dental Research vol. 65 Special Issue. 1986.

Dolan, M. M. et al. Abstract 411 Journal of Dental Research vol. 65 Special Issue 1986.

Corner, A. M. et al. Abstract 948 Journal of Dental Research vol. 65 Special Issue 1986.

Malamud, D. et al. Abstract 949 Journal of Dental Research vol. 65 Special Issue 1986.

Linstedt, M. Antimicrobial Agents and Chemotherapy 34(10): 1949–1954 (1990).

Bowers, B. "A Biotech Worker Pursues Formula for Success" Wall Street Journal, Jan. 30, 1991.

Lang, J. Dental Research, 65:246 91986) abst. No. 689.

Löe, J. Periodontal Research, 11:135–144 (1976).

Chem. Abst., 101, 279 (1984) Abst. No. 28100k.

Jefopaulos, Dentifrices, 1970, Noyes Data Corp., Park Ridge, N.J. pp. 65–67.

Remington's Pharmaceutical Sciences, 1975, pp. 335–337.

VISCOUS SURFACTANT EMULSION COMPOSITIONS

This is a continuation-in-part application of U.S. patent application Ser. No. 07/673,631 filed Mar. 22, 1991 now U.S. Pat. No. 5,244,652 and U.S. patent application Ser. No. 07/673,784 filed Mar. 22, 1991 now U.S. Pat. No. 5,314,917.

The present invention relates to novel hydrophobe-containing viscous surfactant compositions that are stable emulsions and have anti- infective activity. This invention also relates to novel hydrophobe-containing viscous surfactant compositions that are stable emulsions and have spermicidal activity. In particular, the invention relates to compositions that are stable oil-in-water or water-in-oil emulsions. More particularly, the invention is concerned with compositions comprising betaines and amine oxides, substantially nonpolar hydrophobic materials and water soluble, nonionic, cationic or amphoteric materials that act as emulsion aids. The compositions of this invention are of special value for cosmetic, dermatological and pharmaceutical preparations. Compositions of this invention can be used to prepare hair and body shampoos, cleansers, spermicides, dentrifices and compositions for wound healing.

DESCRIPTION OF THE PRIOR ART

Compositions of betaines and amine oxides having antimicrobial activity are known from U.S. Pat. Nos. 4,062,976 (Michaels); 4,075,350 (Michaels); 4,107,328 (Michaels); 4,145,436 (Michaels) 4,183,952 (Michaels), 4,839,158 (Michaels) and U.S. patent application Ser. Nos. 07/673,631 and 07/673,784.

Applicant sought to prepare stable emulsions of betaines and amine oxides having good antiinfective and/or spermicidal properties using hydrophobic materials.

U.S. patent application Ser. No. 07/673,631 issuing as U.S. Pat. No. 5,244,652 on Sep. 14, 1993, discloses in Example 21 creme formulations comprising C31G (amphoteric surfactant compositions of alkyl betaines and alkyl amine oxides), Type A gelatin, glycerine, hydroxyethyl cellulose and water. Example 23 of U.S. patent application Ser. No. 07/673,631 discloses an ointment for xeroderma comprising C31G, Type A gelatin, glycerine, hydroxypropyl cellulose and petroleum jelly.

It has been found that amphophilic hydrophobic materials such as Tween 80 (HLB 15) (HLB is hydrophilic/lipophilic balance number), a polyoxyethylene derivative of mono fatty esters of sorbitol is not a suitable hydrophobic materials as it neutralizes the antiinfective properties of the betaine and amine oxide compositions of U.S. Pat. Nos. 4,062,976, 4,075,350, 4,107,328, 4,145,436, 4,183,952 and 4,839,158. It is also known that Tween 80 (HLB 15) is unsuitable as it is used to neutralize quaternary ammonium disinfectants. A 3:1 ratio of Tween 80 to a 0.5% solution of the betaines and amine oxides of this disclosure inactivated the antimicrobial effect of these betaines and amine oxides. Compositions containing combinations of betaines and amine oxides exhibited antimicrobial activity at a 30:1 ratio of the hydrophobic material isopropyl myristate to the betaines and amine oxides. Brij 78 (HLB 15.3) a polyoxyethylene ether of fatty alcohols decreases the antiinfective properties of the aforementioned betaine and amine oxide compositions.

Applicant has found that hydrophobic materials that are self-emulsifying or that are good emulsifiers deactivate the antiinfective activity of the surfactant formulations of this disclosure. In general, such deactivating hydrophobic materials will have an HLB value greater than 1 and lower than cleansers which generally have HLB's of 25 or higher such as natural or synthetic soaps.

Applicant has now found that certain substantially nonpolar hydrophobic materials typically having a HLB value of 1 or less when combined with the surfactant formulations of this disclosure and emulsion aids create stable emulsions which have antiinfective activity. The expression "surfactant formulations of this disclosure" means these amphoteric betaine and amine oxide compositions of U.S. Pat. Nos. 4,062,976, 4,075,350, 4,107,328, 4,145,436, 4,183,952, 4,839,158 and U.S. patent applications Ser. Nos. 07/673,631 and 07/673,784 and the amphoteric betaine and amine oxide surfactant compositions disclosed in the specification of the present application. The expression "C31G" (registered trademark) is defined as a surfactant composition of "alkyl betaines and alkyl amine oxides."

Accordingly, a primary object of the present invention is to provide stable emulsions containing hydrophobic materials having antiinfective properties.

A further object of the present invention is to provide stable emulsions containing hydrophobic materials having spermicidal properties.

Another object of the invention is provide compositions that are easily applied and promote skin integrity.

Still another object of this invention is to provide compositions that are less irritating to mammalian tissues or cells than the usual surfactants used for cleaning or disinfecting.

Yet another object of this invention is to provide compositions of surfactant formulations of this disclosure that can be used for antiinfective or disinfection purposes at higher concentrations or for longer periods of time than other previously known compositions containing betaines and amine oxides.

A further object of this invention is to provide compositions that aid in wound healing and can be used to treat damaged skin, and prevent desiccation of traumatized tissue.

SUMMARY OF THE INVENTION

It has now unexpectedly been found that compositions comprising the surfactant formulations of this disclosure (as hereinbefore defined); substantially nonpolar hydrophobic materials typically having a HLB value of 1 or less and water soluble, nonionic, cationic or amphoteric, emulsion aids that increase viscosity and do not deactivate the antiinfective activity of the surfactant formulations of this disclosure, form stable emulsions having antiinfective activity. Compositions according to this invention may also have spermicidal activity. An emulsion is considered to be stable when the emulsion, either oil-in-water or water-in-oil, does not separate into separate phases under normal conditions of storage and use.

Applicant has discovered that the use of substantially nonpolar hydrophobic materials and emulsion aids provides surfactant formulations of this invention having useful emolliency effects and decreased dermal toxicity over known preparations used in cleansing or disinfection. Compositions according to this invention have improved adherence to the skin.

In accordance with this invention stable emulsions having finer particle sizes are prepared in minutes as compared to the prior art where emulsions having fine particle sizes are prepared in hours, and still may not be stable. Emulsions according to this invention may also have good foaming properties often essential to assure adequate use of cleansers.

DETAILED DESCRIPTION OF THE INVENTION

This invention overcomes a problem in the art, namely to create emulsions such as cleansers, lotions, ointments, cremes, jellies and gels that are stable and exhibit antiinfective activity.

The emulsion compositions of this invention comprise the surfactant formulations of this disclosure (as defined above); substantially nonpolar hydrophobic materials typically having a HLB value of 1 or less and water soluble nonionic, cationic or amphoteric emulsion aids that increase viscosity and do not deactivate the antiinfective activity of the surfactant formulations of this disclosure. The materials used in this invention should be dermatologically and/or pharmaceutically acceptable depending on the intended use of the final composition.

The surfactant formulations of use in the present invention include those of the type disclosed in U.S. Pat. Nos. 4,062,976, 4,075,350, 4,107,328, 4,145,436, 4,183,952, 4,839,158, 5,244,652 and 5,314,917, the subject matter of each of which is incorporated herein by reference and the surfactant formulations disclosed in the present application. The betaines used in this invention are selected from the group consisting of alkyl-N-betaines, alkyl amido ethyl betaines, alkyl amido propyl betaines, alkyl sultaines, alkyl amido propyl hydroxy sultaines, alkyl hydroxy propyl sultaines, alkyl-N-sulfobetaines, acyl-N-betaines and mixtures of two or more thereof. The amine oxides used in this invention are selected from the group consisting of alkyl-N,N-dimethylamine oxides, alkyl-N,N-dihydroxyethylamine oxides, acylamide t-amine oxides and mixtures of two or more thereof. The alkyl and acyl groups of such betaines and sulfobetaines typically contain from 10 to 18 carbon atoms, preferably from 12 to 16 carbon atoms.

Typically, the betaine and amine oxide components are present in a molar ratio of from 1:5 to 5:1, preferably in a molar ratio of from 1:3 or 3:1, and more preferably in a molar ratio of 1:1. Examples of betaines that can be used in this invention are: coco-N-betaine, cetyl-N-betaine, stearyl-N-betaine, isostearyl-N-betaine, oleyl-N-betaine, lauryl-N-betaine; myristyl-N-betaine coco-N-sulphobetaine, cetyl-N-sulphobetaine, stearyl-N-sulfobetaine, isostearyl-N-sulfobetaine, oleyl-N-sulfobetaine,; myristylamido-N-betaine, cocoamido-N-betaine, cetylamido-N-betaine, stearylamido-N-betaine, myristyl-N-sulphobetaine, isostearylamido-N-betaine, and oleyl-amide-N-betaine.

When used here the term "coco" is that used in the CTFA (designations of Cosmetic and Toiletry and Fragrance Association, Was., D.C.) and is used to indicate alkyl groups present in coconut oil, i.e. a mixture of alkyl groups of from 10 to 18 carbon atoms. The designations of the compounds listed herein are those of the CTFA.

Exemplary of the amine oxides used in this invention are: decyl-N,N-dimethylamine oxide, lauryl-N,N-dimethylamine oxide, lauramine oxide, myristamine oxide, stearyl-N-N-dimethylamine oxide, oleyl-N,N-dimethylamine oxide., coco-N,N dihydroxyethylamine oxide, cetyl-N,N-dihydroxyethylamine oxide, oleyl-N,N-dihydroxyethyl-amine oxide, N,N-dihydroxyethylamine oxide, oleyl-N,-N-dihydroxyethyl-amine oxide and mixtures of the same.

The hydrophobic materials used in this invention are substantially nonpolar hydrophobic materials. Typically, the hydrophobic materials have an HLB value of 1 or less. The hydrophobic materials used in this invention can be esters or ethers of long chain alkyl alcohols or polyhydric alcohols having no free hydroxyl groups. Hydrophobic materials that can also be used in this invention are isopropyl myristate, coconut oil, peanut oil, palm oil, mineral oils, paraffin oils and other highly saturated oils, trialkylates of glycerin, waxes, animal, mineral and vegetable waxes, high molecular weight oils, mixtures of waxes and oils, petrolatum, and lanolin. Mixtures of hydrophobic materials can be used. Fatty alcohols such as cetyl alcohol can also be used as a hydrophobic material, although cetyl alcohol does decrease slightly the antiinfective properties of the surfactant formulations of this disclosure. In general, the use of anionic fatty acids such as coco fatty acid and stearic acid or soaps of these fatty acids, and sulfates and sulfonates should be avoided as it is expected that they will inactivate the antiinfective actions of the surfactants of this disclosure. However, if the surfactants of this disclosure are present in a high enough concentration it may be possible to use one or more of these anionic components at low concentrations without inactivating the antiinfective activity of the surfactants of this disclosure.

The compositions of this invention include water soluble, nonionic, cationic or amphoteric, natural or synthetic emulsion aids that increase viscosity and do not deactivate the antiinfective activity of the surfactant formulations of this disclosure. Examples of such emulsion aids are polyhydric alcohols, gelatin and cellulose gums. These emulsion aids and other emulsion aids will be described below.

Polyhydric alcohols are used to make viscous creams, lotions and pastes. Illustrative of the polyhydric alcohols useful in this invention are ethylene glycol, glycerine, propylene glycol, polyethylene glycols such as the carbowaxes (trademarks), xylitol, sorbitol, and mannitol.

Low molecular weight monohydric alcohols that modify viscosity and aid in penetration of the surfactant formulations of this disclosure into the skin are useful in this invention. Isopropanol and ethanol are useful.

Cellulose gums useful in this invention are high molecular weight nonionic gums such as methyl, hydroxyethyl, hydroxypropyl, and hydroxypropylmethyl cellulose. Hydroxylated or methylated cellulose gums can be used. Polymers that may be used in place of the cellulose gums are synthetic materials having some properties analogous to said gums such as polyvinyl alcohol, polyvinyl pyrrolidone and some nonionic polyacrylic acid polymers (such polymers are herein referred to as synthetic equivalents of cellulose gums). Cationic gums such as the polyquaterniums and cationic guar gums can be used in the composition of this invention. Hyaluronic acid and starch derivatives (hydrolyzed starches) are examples of other materials that can be used. Protein based fat replacements or derivatives of starch that can be used as fat replacements such as a hydrolyzed mixture of amylose and amylopectin or maltopectin may also be used.

Gelatin and/or pectin can be used in these compositions. Gelatin, a high molecular weight preparation of hydrolyzed collagen has inherently low viscosity under conditions where it is not forming rigid gels.

Type A and Type B gelatins can be used in this invention. Type A gelatins have isoelectric points between pH 7 and 9. Type B gelatins have isoelectric points between pH 4.6 and 5.2. Type B gelatins become cloudy at the isoelectric point and have limited use at low pH. The gelatins most useful in this invention will have Bloom strengths of about 100 to 300, and may have average molecular weights from about 25,000 to 300,000.

Pectin can be used in addition to or as an alternative to gelatin in the compositions of this invention. Pectin is a high molecular weight hydrocolloidal substance (polyurinade) related to carbohydrates and found in varying proportions in fruits and plants. Wheat proteins such as hydrolyzed whole wheat protein and vegetable proteins are also useful as emulsion aids.

In a preferred embodiment of this invention, gelatin, cellulose gums, and glycerin are used as co-emulsion aids.

The operating pH of the composition is 4.0 to 7.0, preferably, from about 4.5 to 6.5. In general, the acid used to the supply the required pH can be any organic or inorganic acid, such as hydrochloric acid, phosphoric acid, sulfuric acid, citric acid, acetic acid, tartaric acid or nicotinic acid. Acids with high buffering capacity are preferred.

Compositions of this invention can formulated as shampoos, cleansers, lotions, ointments, cremes, jellies, gels, foams, and suppositories. Compositions of this invention can be used to prepare hair and body shampoos, cleansers, spermicides, contraceptive devices, dentrifices, compositions for wound healing, dressings, surgical scrubs and moisturizers.

Preferred compositions of this invention contain generally the following components in aqueous and nonaqueous phases of water-in-oil or oil-in-water emulsions:
 0.1–10% Active ingredient amphoteric surfactant of betaines and amine oxides of this disclosure;
 0.5–90% hydrophobic materials; and
 1–25% emulsion aids.

More preferred compositions of this invention contain generally the following components in aqueous and nonaqueous phases of water-in-oil or oil-in-water emulsions:
 0.1–10% Active ingredient amphoteric surfactant of betaines and amine oxides of this disclosure;
 0.1–10% nonionic and/or cationic cellulose gums or synthetic analogs thereof;
 0–4% gelatin;
 0–3.0 pectin;
 1–15% polyhydric alcohols and
 0.5–90% hydrophobic materials.

Compositions of this invention are readily prepared by one skilled in the art. The amphoteric surfactants are premixed. In general the gums are hydrated and dissolved in part of the water used. The polyhydric alcohols may be used for trituration of the gums if necessary. The premixed surfactants are added to the hydrated gums. The hydrophobic material is combined with the aqueous phase. If necessary, high shear mixing is used.

A fuller understanding of the present invention will be gained from the following illustrative examples.

EXAMPLE 1–5

Amphoteric surfactant formulations that can be used in preparing the compositions of this invention:
 Lauryl Betaine (30% AI) 1000 pts
 Lauramine Oxide (30% AI) 809 pts
 Citric Acid monohydrate 63 pts
 Purified water 100 pts The above are stirred to a uniform solution. At a dilution of one part to 30, the composition should have a pH of 4.85 at the glass electrode. Putative concentration equal to 27.5% active ingredients (ai).

EXAMPLE 2

Cetyl betaine 20% AI: 200 lbs
Myristamine oxide 30% AI: 95 lbs
Citric acid monohydrate: 6.8 lbs
Purified water: 100 lbs.
Prepare as in Example 1
To make about 402 lbs at 17% AI, at dilution 1% AI; pH 4.9.

EXAMPLE 3

Coco amido propylbetaine 30% AI: 530 lbs
Cocoamido propylamine oxide 30% AI: 470 lbs
Citric acid monohydrate, USP 60 lbs
Purified water, USP: 100 lbs
Prepare as in Example 1
To make about 1160 lbs at 25.9% AI at a dilution 1% AI,: pH-4.9.

EXAMPLE 4

Cocohydroxypropyl sultaine, 30% AI: 347 lbs
Cocoamine oxide 30% AI: 240 lbs
Citric acid monohydrate 24 lbs
Purified Water 100 lbs
Prepare as in Example 1
To make about 711 lb at about 24.8% AI at a dilution 1% AI, pH-5.0.

EXAMPLE 4A

Coco hydroxy propyl sultaine 30% AI: 76.5 g
laurylamine oxide 30% AI: 36.5 g
citric acid monohydrate 9.1 g
Purified water 40 g
Prepare as in Example 1

EXAMPLE 5

Cocoamido-2-hydroxypropyl sultaine 30% AI: 89 g
Laurylamine oxide 30% AI: 36.5 g
citric acid monohydrate 13 g
NaOH 0.3 g
Purified water 40 g
Prepare as in Example 1 The emulsions of Examples 6–14 were prepared using a manual pump homogenizer.

EXAMPLE 6–8

The following protocol was used to test the antiinfective properties of the listed compositions:
Type of Experiment: MIC (Minimum Inhibitory Concentration)
Title: C31G Cream Formulations vs. E. coli
Bacteria: E. coli
Method:
 Set up 10 test tubes for each bacteria, to be tested against the agent. First tube contains 4.5 ml of media (TSB or BHI), pH 5.2. In the following 9 tubes put 2.5 ml. Add 0.5 ml of agent (using 5% as working solution)

to be tested, so the total volume in the first tube is 5.0 ml. Transfer 2.5 ml to the second tube and mix well and continue transferring 2.5 ml until last tube. Discard the last 2.5 ml. Add 0.1 ml of bacteria to each tube (1 ml frozen bacteria in 10 ml media). Incubate at 37° C. over night.

|  | Ex 6 | Ex 7 | Ex 8 |
| --- | --- | --- | --- |
| Surfactant % (C31G of Example 1) | 0.5 | 0.5 | 0.5 |
| Gelatin % | 0.75 | 0.75 | 0.75 |
| Hydroxypropylmethyl cellulose % | 0.5 | 0.5 | 0.5 |
| Propylene Glycol % | 10 | 10 | 10 |
| Tartaric Acid % | 0.06 | 0.06 | 0.06 |
| Isopropyl myristate % | 5.0 | 10.0 | 15.0 |
| H$_2$O to 100% |  |  |  |
| MIC for E. Coli (ppm) | 40 | 60 | 80 |
| MIC for C31G of Example 1 = 80 ppm |  |  |  |

EXAMPLES 8A–15

Type Of Experiment: MIC (Minimum Inhibitory Concentration)
Title: C31G Cream Formulations vs. S. Aureus
Bacteria: S. Aureus
Method:
Set up 10 test tubes for each bacteria, to be tested against each agent. First tube contains 4.5 ml of media (TSB or BHI), pH 5.0. In the following 9 tubes put 2.5 ml. Add 0.5 ml of agent (using 5% as working solution) to be tested, so the total volume in the first tube is 5.0 ml. Transfer 2.5 ml to be second tube and mix well and continue transferring 2.5 ml until you get to the last tube. Discard the last 2.5 ml. Add 0.1 ml of bacteria to each tube (1 ml previously frozen bacteria in 10 ml media). Incubate at 37° C. overnight.
Conclusion:
Results vs. S. Aureus shown in the table below
Type of Experiment: Zone of Inhibition
Title: zone of Inhibition Testing on C31G Creams
Bacteria: E. Coli
Drug Concentration: 0.5% C31G Formulations and dH$_2$O.
Method:
Set up the plates (TSA or BHI), using 7.0 ml of the media (pH 7.2), with 8.0 ml of the seed layer on top. (1000 ml of media with 10 ml of bacteria). Put 4 sterilized pads on each plate and add 0.01 ml of the drug (using 5% as our working solution) to be tested. Incubate at 37° C. over night. Measure the zone next day.
Results vs. E. Coli shown in the Table below

| Formulation | MIC (ppm) | Mean Zone of Inhibition (mm) |
| --- | --- | --- |
| Ex. 8A C31G 0.5%, Tartaric Acid 0.06%, Gelatin 0.75%, HPMC 0.5%, Isopropyl Myristate 15%, Propylene Glycol 12%, Purified H$_2$O to 100% | 80 | 10.75 |
| Ex. 9 C31G 0.5%, Tartaric Acid 0.06%, Gelatin 0.75%, HPMC 0.5%, Isopropyl Myristate 15%, Propylene Glycol 10%, Purified H$_2$O to 100% | 160 | 10.25 |
| Ex. 10 C31G 0.5%, Tartaric Acid 0.06%, Gelatin 0.75%, HPMC 2%, Isopropyl Myristate 5%, Propylene Glycol 10%, Purified H$_2$O to 100% | 40 | 12 |
| Ex. 11 C31G 0.5%, Tartaric Acid 0.06%, Gelatin 0.75%, HPMC 0.5%, Isopropyl Myristate 10%, Propylene Glycol 12.0%, Purified H$_2$O to 100% | 80 | 11 |
| Ex. 12 C31G 0.5%, Tartaric Acid 0.06%, Gelatin 0.75%, HPMC 0.5%, Isopropyl Myristate 5%, Propylene Glycol 12.0%, Purified H$_2$O to 100% | 80 | 11.25 |
| Ex. 13 C31G 0.5%, Tartaric Acid 0.06%, Gelatin 0.75%, HPMC 2.5%, Isopropyl Myristate 5%, Propylene Glycol 10%, Purified H$_2$O to 100% | 80 | 10.5 |
| Ex. 14 C31G 0.5%, Tartaric Acid 0.06%, Gelatin 0.75%, HPMC 2%, Isopropyl Myristate 10%, Propylene Glycol 10%, Purified H$_2$O to 100% | 80 | 12 |
| Ex. 15 0.5% C31G (control) | 60 | 12.5 |

EXAMPLES 16–23

The following are examples of stable water-in-oil emulsions prepared as anti-infective ointments for use as barrier creams, for use on wounds, burns or other sanitizing purpose.
The aqueous phase in all of these examples comprise:

Example 16

Aqueous Phase
C31G of Example 1 diluted to 5% actives
0.8 Pts. Hydroxypropyl cellulose, high viscosity [HPC]
1.25 Pts. Gelatin type A100
2.0 Pts. Glycerin U.S.P.
The gums were triturated with the glycerin and then hydrated by stirring into about 50 points purified water at 60° C. to disperse and then hydrated while cooling to ambient temperature. 18.2 pts of the C31G diluted with 27.25 parts of water are added to equal 100 pts of the aqueous phase.

Example 17

Aqueous Phase
C31G of Example 1 to be diluted to 5% actives with purified water. No excipients were added.
The viscous aqueous solution of surfactant with the excipients of Example 16 was used for the following emulsion preparations, using the following method.
A laboratory colloid mill (Silverson Homogenizer Model L2R) is mounted over a tall form 350 ml beaker in a water bath with the base of the rotor assembly 5 mm above the bottom of the beaker. 80 grams of the oil phase and 20 grams of the aqueous phase are placed in the beaker and prewarmed to 40° C. in the water bath and the colloid mill lowered into the beaker in the water bath. The homogenizing is started using 50 volts to control the operating speed so as not to overheat the HPC which can precipitate above 43° C. After homogenizing for 10 minutes at temperatures between 40°–43° C. ice is added to the bath and mixing continued to bring the temperature to below 30° C. This procedure was used with various lipids to form the following stable water-in-oil emulsions having excellent antiinfective properties. This was shown using a modification of the zone of inhibition studies shown above. The modification comprises smearing 0.05 grams of the ointment on the paper disk and pressing the disc, ointment side down, on the prepared streaked plate.

|  | Lipid Phase | Aqueous Phase | Zone of Inhibition |
|---|---|---|---|
| Example 18 | Petrolatum U.S.P. | Example 16 | 16.5 mm |
| Example 19 | Glycerol Tripalmitate | Example 16 | 16 mm |
| Example 20 | Coconut Oil | Example 16 | 17 mm |
| Example 21 | Mineral Oil | Example 16 | 16 mm |

Note: the control using 0.1 ml of a .5% C31G solution of Ex. 1 was 17.5 mm in the zone of inhibition protocol.

The procedure of Example 20 was modified using the aqueous phases of Examples 16 and 17 but diluted to 2.5% actives to determine the comparative effect of the excipients on the emulsion stability of the coconut oil at reduced surfactant concentration.

|  | Lipid Phase | Aqueous Phase |
|---|---|---|
| Example 22 | Coconut Oil | As Example 16 with the C31G diluted to 2.5% |
| Example 23 | Coconut Oil | As Example 17 with the C31G diluted to 2.5% |

Results: The water in oil emulsions formed after the homogenization and cooling were observed. The product of Example 22 was stable at ambient temperatures of 85°–90° for 14 days and to date.

The emulsion of Example 23 appeared uniform during packaging but when observed after four hours showed about 20% by volume of an aqueous phase had separated. This indicates the value of the combined excipients in modifying the emulsification character of the agent with this lipid.

In the following examples the procedures of homogenization used above in making water-in-oil emulsions were used as a preliminary stage in preparing fine grained oil-in-water emulsions by inverting the water-in-oil emulsion to an oil-in-water emulsion.

In examples 23A and 23B which follow the aqueous phases of examples 16 and 17 are used. A medium viscosity, 70 weight Saybolt, NF, mineral oil was used for the oil phase.

The preliminary preparation of the water-in-oil emulsion produced exactly as for the homogenization in Examples 18 to 21 above. However, instead of cooling, the aqueous phase was gradually increased to 120 grams by adding 100 grams in three equal portions over a 15 minute period and then cooling the emulsion while continuing mixing until the temperature decreased to below 30° C. The following are the compositions of the phases of the formulation with ratios of 20/120 in the oil/water phases.

|  | Lipid Phase | Aqueous Phase |
|---|---|---|
| Example 23A | mineral oil 70 wght. | Example 16 |
| Example 23B | mineral oil 70 wght. | Example 17 |

For age testing of stability judgements were made by observation over the noted time periods at ambient temperatures of 30° C., and at 43° C. An additional observation was performed on dilutions of the above o/w emulsions. The dilutions were made in pure water using 5% of the above examples and storing the preparations at ambient temperature as above.

Results: Age Test separation (visual) as % of total volume

| Temperature/Time | Ex 23A (with excipients) | Ex 23B (no excipients) |
|---|---|---|
| Ambient 48 hours | no separation | 25% (bottom) |
| Ambient 10 days | no separation | 25% (bottom) |
| 43° C. - 14 hours | 5% bottom (cloudy) | 35% (bottom) |

Note: Bottom separation is a clear aqueous phase and top separation is cream unless otherwise noted.

| | Ex 23 (A) diluted | Ex 23 (B) diluted |
|---|---|---|
| Ambient 20 hours | no separation | 28% (bottom), 8% (top) |
| Ambient 10 days | no separation | 35% (bottom), 5% (top) |

Type Of Experiment: Zone Of Inhibition
Title: C31G Formulations—mixed 1:1 with different chemicals; in
order to identify inactivators.
Bacteria: S. sanguis M5.
Drug Concentration: 0.5% C31G Formulations, and purified water.
Method:
Set up the plates (TSA or BHI), using 7.0 ml of the media (pH 7.2), with 8.0 ml of the seed layer on top. (1000 ml of media with 10 ml of bacteria). Put 4 sterilized pads on each plate and add 0.01 ml of the drug (using 5% as working solution) to be tested. Incubate at 37° C. overnight. Measure the zone next day.

| Ingredient | Conc. | C31G Conc. | Mean Zone |
|---|---|---|---|
| POE(5) Oleyl ether | 5% | 0% | 0 |
| POE(5) Oleyl ether | 5% | 0.5% | 0 |
| Sorbitol 70% | 5% | 0% | 0 |
| Sorbitol 70% | 5% | 0.5% | 12 |
| Glycerin | 5% | 0% | 0 |
| Glycerin | 5% | 0.5% | 12 |
| Brij 78 | 5% | 0% | 0 |
| Brij 78 | 5% | 0.5% | 9.5 |
| PEG 400 | 5% | 0% | 0 |
| PEG 400 | 5% | 0.5% | 11.25 |
| TEA Stearate | 5% | 0% | 0 |
| TEA Stearate | 5% | 0.5% | 0 |
| Pluronic Acid F-68 | 5% | 0% | 0 |
| Pluronic Acid F-68 | 5% | 0.5% | 10 |
| Gelatin (B) | 0.2% | 0% pH 7.4 | 0 |
| Gelatin (B) | 0.2% | 0.5% pH 7.4 | 12 |
| HPMC | 0.2% | 0% | 0 |
| HPMC | 0.2% | 0.5% | 11 |
| C31G | — | 0.5% | 12.25 |
| dH$_2$O | 100% | 0% | 0 |

Discussion: POE(5) oleyl ether has a HLB of 8.2 and completely inactivated C31G. Compounds showing partial inhibition are Brij 78 having a HLB of 15 and Pluronic Acid F68 has a HLB of 24. The anionic soap triethanolamine stearate, also showed complete inhibition of C31G activity. The hydrophilic gums, gelatin and polyhydroxy alcohols showed no inhibition of C31G activity.

EXAMPLE 25-30

Example 25

0.5% C31G of Example 1
0.06% tartaric acid
1.25% gelatin

Example 26

Composition of Example 25 with 15% isopropyl myristate, and H₂O to 100%

Example 27

Composition of Example 25 with 15% isopropyl myristate, 4% cetyl alcohol and H₂O to 100%

Example 28

Composition of Example 25 with 15% isopropyl myristate, 4% stearic acid and H₂O to 100%

Example 29

Composition of Example 25 with 20% isopropyl myristate, 4% Brij 78, 4% cetyl alcohol and H₂O to 100%

Example 30

Composition of Example 25, with 20% isopropyl myristate, 4% stearic acid and H₂O to 100%

| Formulations | MIC (in ppm) | | Zone of Inhibition (in mm) | | | Stability |
|---|---|---|---|---|---|---|
| | E. coli | A. viscosis | S. sanguis | A. viscosis | S. mutans | |
| Ex. 26 | 150 | 30 | 80 | 17 | 16 | stable |
| Ex. 27 | 500 | — | 160 | 11 | 8 | stable |
| Ex. 28 | >2500 | — | >160 | 0 | 0 | not stable |
| Ex. 29 | >2500 | — | 160 | 12 | 9 | stable |
| Ex. 30 | >2500 | 120 | >160 | 9.5 | 9.5 | not stable |
| C31G (0.5%) | 120 | — | 30 | 19 | 18 | — |

Example 31

Suppositories
4–8%—gelatin type A 100–300 Bloom
5–20%—glycerin U.S.P.
5.9–17%—C31G of Example 2
0.5–2%—hydroxypropyl methyl cellulose;
3–8%—triacyl glycerols; and water, pure to 100%

The gums are hydrated in water, the C31G dissolved and the triacyl glycerols homogenized at 50° C. and cooled to about 40° C. and poured into mold to cool and form a firm gel.

I claim:

1. A water-in-oil or oil-in-water emulsion comprising an amphoteric surfactant solution comprising
   i) a mixture of a betaine selected from the group consisting of alkyl-N-betaines, alkyl amido ethyl betaines, alkyl amido propyl betaines, alkyl sultaines, alkyl amido propyl hydroxy sultaines, alkyl hydroxy propyl sultaines, alkyl-N-sulfobetaines and acyl-N-betaine or mixtures of two or more thereof and an amine oxide selected from the group consisting of alkyl-N,N dimethylamine oxides, alkyl-N,N-dihydroxyethylamine oxides and acylamide t-amine oxides or mixtures of two or more thereof;
   ii) a pharmaceutically or dermatologically acceptable substantially nonpolar hydrophobic material having a HLB value of 1 or less and
   iii) at least one water soluble, pharmaceutically or dermatologically acceptable nonionic, cationic or amphoteric emulsion aid.

2. A composition according to claim 1 wherein the hydrophobic material is selected from the group consisting of isopropyl myristate, coconut oil, peanut oil, palm oil, mineral oils, paraffin oil, trialkylates of glycerin, highly saturated oils, animal waxes, mineral waxes, vegetable waxes, high molecular weight oils, petrolatum and lanolin-or-mixtures thereof.

3. A composition according to claim 1 wherein the emulsion aids have a HLB value of greater than 25.

4. A composition according to claim 1 wherein the emulsion aids are selected from the group consisting of gelatin, pectin, alkyl polyhydric alcohols, alkyl monohydric alcohols, cellulose gums or synthetic analogs thereof, cationic gums, hyaluronic acid and starch derivatives or mixtures thereof.

5. An emulsion according to claim 4 wherein the emulsion aid comprises at least one member of the group consisting of gelatin and cellulose gums and at least one polyhydric or monohydric alcohol.

6. A composition according to claim 4 wherein the emulsion aid is a combination of gelatin, cellulose gum and polyhydric alcohol.

7. A composition according to claim 1 comprising
0.1–10% amphoteric surfactant of betaines and amine oxides;
1–25% emulsion aids; and
0.5–90% hydrophobic materials.

8. A composition according to claim 1 comprising
0.1–10% amphoteric surfactant of betaines and amine oxides,
0.1–10% nonionic and/or cationic cellulose gums or synthetic analogs thereof;
0–4% gelatin;
0–3% pectin;
1–15% polyhydric alcohols;
0.5–90% hydrophobic materials.

9. A composition according to claim 1 wherein the hydrophobic material is an ester or ether of long chain alkyl alcohols wherein there are no free hydroxyl groups in the ester or ether.

10. A composition according to claim 1 wherein the hydrophobic material is an ester or ether of long chain alkyl polyhydric alcohols wherein there are no free hydroxyl groups in the ester or ether.

* * * * *